| United States Patent [19] | [11] | 4,119,629 |
|---|---|---|
| Miller | [45] | Oct. 10, 1978 |

[54] CERTAIN AZAPHENOXATHIIN COMPOUNDS

[76] Inventor: Richard Foster Miller, P.O. Box 743, Sugar Land, Tex. 77478

[21] Appl. No.: 833,049

[22] Filed: Sep. 14, 1977

Related U.S. Application Data

[63] Continuation-in-part of Ser. No. 825,273, Aug. 17, 1977.

[51] Int. Cl.$^2$ ............................................. C07D 521/00
[52] U.S. Cl. ...................... 260/294.8 B; 260/294.8 A; 260/294.8 G; 260/609 E; 424/256
[58] Field of Search .................................. 260/294.8 B

[56] References Cited

U.S. PATENT DOCUMENTS 3,995,042   11/1976   Yale .............................. 260/294.8 B

*Primary Examiner*—Alan L. Rotman

[57] ABSTRACT

A pharmacological composition useful as potential central nervous system depressants and weight control agents in animals and humans comprising a substituted aromatic Tricyclic and Pentacyclic sulfide wherein the aromatic is phenyl, pyridyl, pyrazidyl, pyrimidyl, and isosteric substitutions including elements in Group VI-a of the Periodic Table.

7 Claims, No Drawings

CERTAIN AZAPHENOXATHIIN COMPOUNDS

This application is a continuation in part of my prior copending application U.S. Ser. No. 825,273, filed Aug. 17, 1977.

The present invention provides substituted aromatic tricyclic and pentacyclic sulfides, a process for their manufacture, and a method of using them in control of central nervous system activity.

More particularly, the present invention relates to substituted aromatic tricyclic and pentacyclic sulfides of the type wherein the aromatic is phenyl, pyridyl, pyrazidyl, pyrimidyl, and isosteric substitutions including elements in Group VI-a of the Periodic Table of Elements.

Numerous methods appear in the prior art for the synthesis of aryl sulfides. These procedures, however, generally suffer from either a lack of applicability or harsh reaction conditions. Further, the synthesis of sulfides from halobenzenes and activated halobenzenes is known as well as the synthesis from dinitrobenzenes. It has now been found, however, that novel extensions of these synthesis include some symmetrically substituted aromatic-sulfides, and the synthesis of non-symmetrically substituted aromatic sulfides through either the displacement of halogens from halonitro benzenes as hereinafter shown in Equation 1, or via preferential halo-sequential nitro displacement as hereinafter shown in Equation 2.

The most significant observation made was that nucleophilic displacement when using a halonitroaromatic system occurred in a selective manner. This novel phenomenon was observed when an exothermic reaction occurred in the solid state, using 1-chloro-2,4-dinitrobenzene and sodium thiophenoxide. Upon further experimentation, it was found that the major product of this reaction was 1-thiophenyl-2,4-dinitrobenzene as seen in Equation 1.

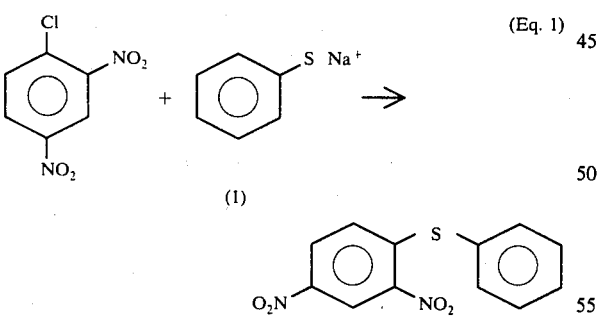

However, it was also discovered than when solvating the halodinitrobenzene in DMF under nitrogen purge at room temperature, adding the sodium thiophenoxide (2:1 molar ratio), and allowing the mixture to react for as long as 36 hours, the formation of isomeric bis (thiophenyl) nitrobenzenes was observed as seen in Equation 2.

From these observations, it was concluded that not only a halogen but also a nitro group was being displaced, probably in the position para to the initial halogen displacement.

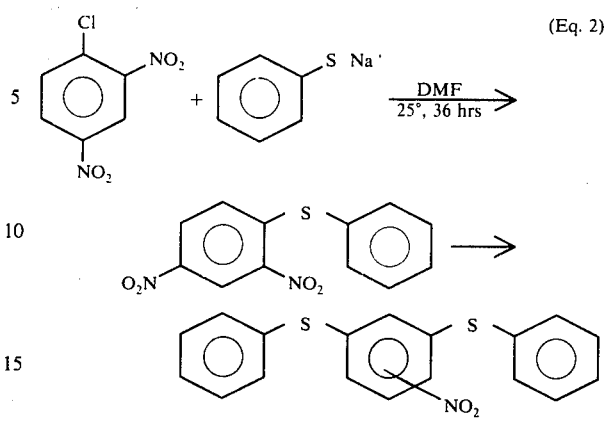

It was also observed that in addition to the displacement of activated halogens by strong nucleophiles such as the thiophenolate ion, similar displacement could be affected with much weaker nucleophiles such as the 2-pyridylmercaptide ion, (2b) shown below.

However, the attempted synthesis of dissymmetric phenylene bisulfides through reaction with sodium thiophenolate, also shown below, failed to give desired products 3 and 4. It however gave, rather unexpectedly, the displacement of the 2-pyridyl moiety to yield 2a below accompanied by phenylene-bisphenyl sulfides 2c and 2e as well as unrelated 2b. It is likely that 2c and 2e arose through nucleophilic displacement of one of the nitro groups following formation of 2a and 2b. Thus,

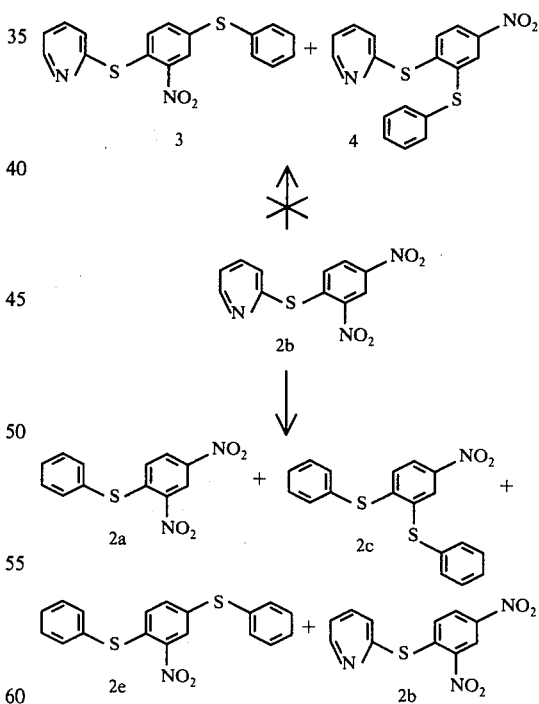

It is interesting to note that the yields of the products obtained by this method are in support of the mechanism proposed for a $S_NAr$ reaction. According to the proposed mechanism, for the 2,4-dihalonitrobenzene, both halogens are activated by the nitro group while for the corresponding 1,4- and 3,4-dihalo-isomers, only one of the halogens is activated. Accordingly, the yields obtained reflect the activation of both halogens for the 2,4-isomer while lower, although equivalent yields, were obtained for the 1,4- and 3,4-isomers, in both of which one halogen is not directly activated.

It should be noted that preparation and isolation of the sodium salts of the desired thios is imperative, as the in situ generation of the sodium thiolates resulted in the isolation of the symmetrical disulfide and unreacted halonitrobenzene. Further, it should also be noted that the addition of the reagents to the DMF in reverse order, or the thiolate as a DMF solution, resulted largely in the production of the disulfide with only minimal quantities of the desired sulfide being produced.

Although hexamethylphosphortriamide (HMPA) has been known to be a superior solvent in which to conduct the nitro-displacement, DMF was found to give adequate yields and to substantially simplify final isolation of the bisulfides.

Attempts to produce the same type of symmetrical bisulfides through an extension of the nitro-displacement procedure previously known to trinitrobenzenes was found to be generally unsatisfactory. By this procedure, the reaction was found to be dangerously exothermal in nature even at −70° and was difficult to control. Further, in addition to the explosive nature of the starting materials required for this potential route, they are also less readily available than the corresponding dihalonitrobenzene, which would severely limit applicability.

EXAMPLE I

To 60 ml of dry distilled DMF, at 0° was added 1 (0.006 mol) and dry nitrogen was bubbled through the solution for 10 minutes. The sodium salt of thiophenol (0.013 mol), as a dry powder, was then added to the reaction which was stirred at 0° for 2.5 hours. The reaction mixture was then chromatographed directly on a silica gel column. The column was eluted with chloroform and the eluate fractions were concentrated to an oily liquid which was crystallized from cold n-hexane.

The following represents initial test observations for one of the above identified compounds.

EXAMPLE II

To 60 ml of dry distilled DMF, at 0° was added 1 (0.012mol). Sodium selenide (0.006 mol), as a dry powder, was then added to the reaction which was refluxed for 21 hours. The reaction mixture was then chromatographed directly on a silica gel column. The column was eluted with chloroform and the eluate fractions were concentrated to an oily liquid which was crystallized from cold n-hexane.

The following represents initial test observations for one of the above identified compounds.

Table of Toxicity Data for
1,5-bis(thiophenyl)-2-nitrobenzene* (2e)

| Test Animal** | Dose (mg/kg im DMSO) | Survival*** Time (Days) |
|---|---|---|
| 1 | 500 | 0 |
| 2 | 250 | 0 |
| 3 | 125 | 0 |
| 4 | 75 | 0 |
| 5 | 50 | 14 |
| 6 | 25 | 2 |

-continued
Table of Toxicity Data for
1,5-bis(thiophenyl)-2-nitrobenzene* (2e)

| Test Animal** | Dose (mg/kg im DMSO) | Survival*** Time (Days) |
|---|---|---|
| 7 | Control | 14 |

*Two minutes after injection, decreased central nervous system activity was observed resulting in death at higher doses. Recovery from CNS depression was noted in animal #5 after 5 days.
**All mice were tail-coded.
***Sacrificed at the end of 14 days.

EXAMPLE III

Synthesis of 1,4-bis(thiophenyl)-2-nitrobenzene (2e).

In an attempt of remedy the problems of solvent contamination experienced with the use of HMPA, the following procedure was carried out. To a reaction flask was added 60 ml of dimethylforamide (DMF) while being purged with nitrogen. To the solvent was added 1-chloro-2,4-dinitrobenzene (1.215 g, 0.006 M) and sodium thiophenoxide (1.584 g, 0.012 M). The reaction was allowed to stir at room temperature for 36 hours. The reaction mixture was partitioned between benzene and water. The organic layer was then dried over anhydrous sodium sulfate. This procedure was wholly unsatisfactory because in partitioning the DMF reaction mixture between benzene and water, the separation was by no means complete. Therefore, a sample was taken and a GC/Mass Spectrogram obtained. A major portion of the reaction material was thought to be the desired product ($M^+$ = 339), 1,4-bis(thiophenyl)-2-nitrobenzene. This material was then chromatographed on an acid-alumina column. Separation was poor for the fraction containing organic material which was aromatic in nature was still contaminated with DMF as shown by an NMR Spectrum.

EXAMPLE IV

Synthesis of 1-thiophenyl-2,4-dinitrobenzene (2a).

To a reaction flask being purged with nitrogen was added 60 ml DMF, 1-fluoro-2,4-dinitrobenzene (1.12 g, 0.006 M) and sodium thiophenoxide (1.584 g, 0.012 M). The resultant mixture was allowed to react for 2.5 hours at 0° and then chromatographed on an acid-alumina column eluted with chloroform. A total of thirteen 100 ml fractions were collected and each fraction then spotted on a thin layer chromatography (tlc) plate. Fractions 1–10 when spotted showed a mixture of three compounds. These fractions were combined and concentrated to a yellow oil. The resultant yellow oil was then chromatographed on a four foot column which had been packed with silica gel 60 (70–230 mesh ASTM). The column was eluted with chloroform. Twelve 100 ml fractions were collected and each fraction spotted on a tlc plate. Fractions 1, 6, and 7 showed no compound. Fractions 2–5 each showed only one spot having the same $R_f$ values. These fractions were then combined, concentrated and recrystallized from cold n-hexane. The resultant yellow crystals were characterized by NMF, ir, and Mass Spectra ($M^+$ = 276). mp = 111°–114°. Yield 87%.

EXAMPLE V

Synthesis and Purification of 1,5-bis(thiophenyl)-2-nitrobenzene

The synthetic procedure followed was as previously mentioned except in the purification of the reaction product. The reaction mixture was chromatographed on a 4 × 117 cm column packed with silica gel (70-230 mesh) and eluted with chloroform. Fourteen 100 ml fractions were collected and spotted on tlc plates. Fractions 1-4 contained no compound while fractions 5-7 contained material which had the same $R_f$ values. Fractions 8-14 contained only DMF. Fractions 5-7 were combined, concentrated, and recrystallized from n-hexane. The bright yellow crystals were characterized by NMR, $13_C$ NMR, ir, and Mass Spectra (M$^+$ = 339). mp = 106°-110°. Yield 72%. Analysis calculated for $C_{18}H_{13}NO_2S_2$: C 63.72, H 3.83, N 4.13, and S 18.88; found C 63.46, H 3.91, N 4.01, and S 19.00.

EXAMPLE VI

Synthesis of 1,5-bis (thiophenyl)-2-nitrobenzene

The synthetic procedure was as previously mentioned for synthesis and purification using 1-nitro-2,4-difluorobenzene (0.95 g, 0.006 M). The reaction product was characterized by NMR, ir, and Mass Spectra (M$^+$ = 339). mp = 111-112.5°. Yield 41%.

EXAMPLE VII

Synthesis of 1,2-bis(thiophenyl)-4-nitrobenzene (2c)

The procedure was as previously mentioned using 1-nitro-3,4-dichlorobenzene (10 g, 0.052 M) and sodium thiophenoxide (13.75 g, 0.104 M). mp = 97°-101°. Yield 31%. The reaction product was characterized by NMR, $13_C$ NMR, ir, and Mass Spectra (M$^+$ = 339).

EXAMPLE VIII

Attempted Synthesis of 1,3-bis(thiophenyl)-5-nitrobenzene

To a reaction flask, which was being purged with nitrogen, was added 60 ml of DMF and 1,3,5-trinitrobenzene (0.050 g, 2 × 10$^{-4}$ M). This reaction mixture was then cooled to −70° with a dry ice acetone bath. Sodium thiophenoxide (0.052 g, 4 × 10$^{-4}$ M) was then added and the previously red solution turned a deep purple as the highly exothermic reaction proceeded. The temperature increased from −70° to +10° within 30 seconds. The reaction was allowed to stir for 2.5 hours. The reaction product was characterized by ir and Mass Spectra (M$^+$ = 213). The only reaction product isolated was 1,3,5-trinitrobenzene.

The following table illustrates utility of the compounds of the present invention as weight control agents.

| Table of Weight Control Observed With 1,5-bis(thiophenyl)-2-nitrobenzene | | | |
|---|---|---|---|
| Animal | Dose (mg/kg) | Weight (grams) | Date |
| #5* | 50 | 16.0 | 7/16/77 |
| | | 15.8 | 7/17/77 |
| | | 16.0 | 7/18/77 |
| | | 16.0 | 7/19/77 |
| | | 16.0 | 7/20/77 |
| | | 16.0 | 7/21/77 |
| #7 | Control | 17.0 | 7/16/77 |
| | | 18.0 | 7/18/77 |
| | | 19.0 | 7/20/77 |
| | | 19.5 | 7/21/77 |

*Animal survived 14-day test period and it was observed that it ingested equal or greater quantities when compared to control.

The closure of derivative 2b was conducted to form the tricyclic 1-azaphenoxathiin. It is known in the prior art that tricyclic compounds are usually less toxic than their open-chain parent compound. When considering optimal sites for substitution, optimal for a chloro-substituent is in the 2-position similar to the chlorpromazine ring system, para to the sulfur of the central ring. On this basis, it is most logical to substitute the proposed 1-azaphenoxathiin in the same position relative to the sulfur, that is either the 3-position or the 7-position. For the sake of synthetic simplicity, the 7-position was selected first.

The synthetic approach to the synthesis of these agents was through the condensation of the disodium salt of 2-mercapto-3-pyridinol with the desired ortho-nitrohalobenzene derivative. Although there are several possible side reactions which are non-productive and serve to decrease the yields of the desired product, these generally were not a significant problem, with the reaction proceeding as shown in Equation 3. Following the synthesis of these compounds, their structure was elucidated and substituent location confirmed by i.r., N.M.R. and mass spectrometry.

EQUATION 3

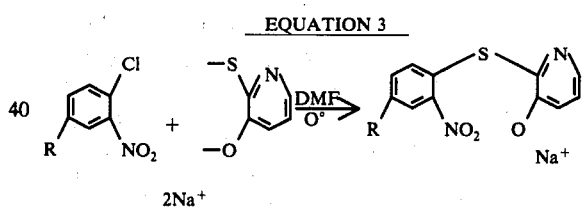

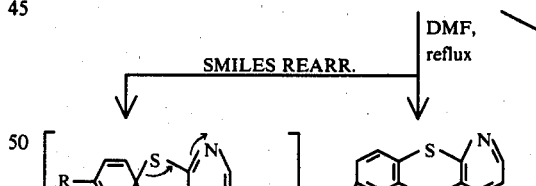

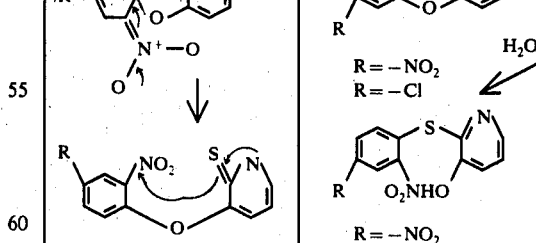

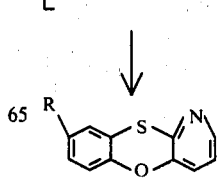

EXAMPLE IX

To a solution of 2.5 g (0.012 mol) of 1-chloro-2,4-dinitro-benzene in 30 ml of dry distilled N,N-dimethylformamide at 0° under dry nitrogen purge, was added 2.052 g (0.012 mol) of 3. The mixture was stirred for 4 hours at 0° and then brought to reflux for 48 hours without prior isolation of the sulfide intermediate. Following completion of the reflux, the reaction mixture was allowed to cool. The aqueous solution was extracted with three 100ml portions of ether which were combined and extracted with three 100ml portions of distilled water. The ether layer was then dried over anhydrous sodium sulfate and concentrated. The resultant oil which did not crystallize was chromatographed over a silica gel column eluted with cyclohexane ethyl acetate (4:1) to yield crude 7-nitro-1-azaphenoxathiin. The crude material was recrystallized from absolute ethanol to give 0.55 g (20% yield). Elemental analysis calculated for $C_{11}H_6N_2O_3S$: C, 53.66, H, 2.44, N, 11.38: found C, 53.76, H, 2.39, N, 11.37.

EXAMPLE X

To a solution of 2.404 g (0.012 mol) of 1-nitro-2,5-dichloro-benzene in 30 ml of dry distilled N,N-dimethylformamide at 0° under dry nitrogen purge, was added 2.052 g (0.012 mol) of 3. The mixture was allowed to stir for 4 hours at 0° and was then brought to reflux for 48 hours. At the end of this period, the mixture was allowed to cool and combined with an equal amount of distilled water. The resultant aqueous solution was extracted with three 100ml portions of ether which were combined and extracted with three 100ml portions of distilled water. The ether solution was dried over anhydrous sodium sulfate powder and then concentrated to an oil and recrystallized from absolute ethanol to give 0.55 g (19% yield) of 7-chloro-1-azaphenoxathiin.

Preliminary testing to determine the toxicity of 7-nitro-1-azaphenoxathiin showed it to have surprisingly low toxicity, with a dose of 100 mg/kg being well tolerated in the test animals. This compound was then subsequently subjected to motor activity testing. These tests were run simultaneously using chloropromazine as a control. This compound was tested at doses of 50, 100 and 200 mg/kg. Further, pharmacologic testing showed the compound had essentially no activity as an anticonvulsant, yet in the temperature depression study the compound significantly depressed temperatures in the test animals from 2.5 to 3.1 degrees over the range of doses tested. It is noted that temperature depression is characteristic of tricyclic CNS agents.

A second analog of this series, 7-chloro-1-azaphenoxathiin was found to be generally well tolerated in test animals with an $LD_{50}$ of approximately 750 mg/kg. Pharmacologic evaluation in both spontaneous and forced motor activity tests showed it to be somewhat more potent than the former. Further, the action of the drug at 200 mg/kg in the spontaneous motor activity test tends to reverse with greater activity observed (47%). An additional set of data was also acquired for this compound which was barbiturate induced sleeping time potentiation. In all cases with 7-chloro-1-azaphenoxathiin there was a prolongation of barbiturate induced sleeping times. Thus, compounds that may be prepared in accordance with Equation 3 above are:

7-chloro-1-azaphenoxathiin
7-nitro-1-azaphenoxathiin
8-chloro-1-azaphenoxathiin
8-nitro-1-azaphenoxathiin
7-trifluoromethyl-1-azaphenoxathiin
7fluoro-1-azaphenoxathiin
7-amino-1-azaphenoxathiin, as well as the 6-, 8-, and 9- substituted analogs.

In addition, the procedure of Equation 3 has been found to be suitable for the preparation of thioxanthones such as 7-chloro-1-azathioxanthone and 7-nitro-1-azathioxanthone.

The following table, when compared with the foregoing table for open chain bisulfide toxicity, shows the marked decrease in toxicity observed with the ring closure feature of the present invention.

Table of $LD_{50}$ Studies of 7-chloro-1-azaphenoxathiin

| Test Animal Group* | Dose (mg/kg) | Survival Time (Days) |
|---|---|---|
| 1 | 50 | 14 |
| 2 | 100 | 14 |
| 3 | 250 | 14 |
| 4 | 500 | 14 |
| 5 | 750 | 0–14** |
| 6 | 1,000 | 0 |
| 7 | 1,500 | 0 |

*All animals were tail-coded
**$LD_{50}$; dependent on the toleration of the animal for this drug several lived the 14-day test period.

The following tables illustrate the effectiveness of various of the compounds of the present invention as central nervous system activity depressants.

| TABLE OF STRYCHNINE ANTICONVULSANT STUDY WITH 7-NITRO-1-AZAPHENOXATHIIN | | | |
|---|---|---|---|
| Test Group | Average Onset Time (min) | Standard Deviation | Standard Error |
| CONTROL (Saline) | 3.10 | 0.0059 | 0.0020 |
| 50 mg/kg | 3.21 | 0.3081 | 0.1086 |
| 100 mg/kg | 3.06 | 0.5681 | 0.1378 |
| 200 mg/kg | 3.06 | 0.8179 | 1.1574 |

| TABLE OF TEMPERATURE DEPRESSION WITH 7-NITRO-1-AZAPHENOXATHIN | |
|---|---|
| Dose | Temperature Depression |
| Control | + 0.72 ± 0.21 |
| 50 mg/kg | − 2.11 ± 0.57 |
| 100 mg/kg | − 3.07 ± 0.57 |
| 200 mg/kg | − 2.71 ± 0.63 |

| 7-CHLORO-1-AZAPHENOXATHIN | |
|---|---|
| Dose | Temperture Depression |
| Control | − 0.21 ± 0.33 |
| 25 mg/kg | − 2.61 ± 0.46 |
| 50 mg/kg | − 2.30 ± 0.32 |
| 100 mg/kg | − 2.70 ± 0.27 |

Table of Barbiturate Sleeping Time Potentiation With 7-Chloro-1-Azaphenoxathiin

| Hexobarbital Sleeping Time Potentiation | | |
|---|---|---|
| Dose (mg/kg) | Mean (min) | SE (min) |
| Control | 58.5 | ± 9.0 |
| 25 | 79.8 | ± 18.0 |
| 50 | 81.9* | ± 5.4 |
| 100 | 104.4* | ± 12.0 |

Barbital Sleeping Time Potentiation

-continued

Table of Barbiturate Sleeping Time Potentiation With 7-Chloro-1-Azaphenoxathiin

| Control | 125.4 | ± 16.9 |
|---|---|---|
| 25 | 120.6 | ± 20.4 |
| 50 | 155.1 | ± 22.1 |
| 100 | 179.5 | ± 22.9 |

*$p < 0.05$

TABLE OF EFFECT OF 7-CHLORO-1-AZAPHENOXATHIIN 100 MG/KG I.P. ON BODY TEMP., HEART RATE, AND RESPIRATION IN RATS

| Time | N | Temp °C | Δ From Veh | H.R. (Beats/Min) | Δ From Veh | Resp (Breath/Min) | Δ From Veh |
|---|---|---|---|---|---|---|---|
| 0 | 5 | 38.5 | — | 331.2 | — | 120.8 | — |
| 30 | 4 | 37.6 | −0.4 | 314.0 | −34.0 | 101.2 | −33.1 |
| 60 | 4 | 36.8 | −2.4 | 288.0 | −36.0 | 79.7 | −65.9 |
| 120 | 4 | 35.8 | −2.4 | 273.0 | −55.0 | 70.0 | −49.2 |
| 180 | 4 | 35.4 | −3.4 | 270.0 | −66.0 | 78.2 | −41.8 |
| 240 | 4 | 35.0 | −3.6 | 289.0 | −51.0 | 82.3 | −33.0 |

It will be apparent from the foregoing that many other variations and modifications may be made in the methods described herein without substantially departing from the essential concept of the present invention. Accordingly, it should be clearly understood that the forms of the invention described herein are exemplary only and are not intended as limitations in the scope of the present invention.

What is claimed is:

1. A compound of the formula:

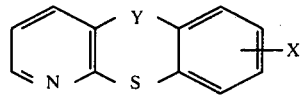

wherein X is an electron withdrawing substituent selected from the group consisting of halogen, $NO_2$, and $CF_3$, and wherein Y is oxygen.

2. A compound of claim 1, 7-nitro-1-azaphenoxathiin.

3. A compound of claim 1, 7-chloro-1-azaphenoxathiin.

4. A compound of claim 1, 7-trifluoromethyl-1-azaphenoxathiin.

5. A compound of claim 1, 8-nitro-1-azaphenoxathiin.

6. A compound of claim 1, 8-chloro-1-azaphenoxathiin.

7. A compound of claim 1, 8-trifluoromethyl-1-azaphenoxathiin.

* * * * *